United States Patent [19]

Hofstetter

[11] 4,356,012
[45] Oct. 26, 1982

[54] MEDICAL LIQUID CONTAINER WITH FILTER VENT

[75] Inventor: Jack H. Hofstetter, Anaheim, Calif.

[73] Assignee: American Hospital Supply Corporation, Evanston, Ill.

[21] Appl. No.: 142,194

[22] Filed: Apr. 21, 1980

Related U.S. Application Data

[63] Continuation of Ser. No. 936,754, Aug. 25, 1978, abandoned.

[51] Int. Cl.³ .............................................. B01D 50/00
[52] U.S. Cl. .................................... 55/385 C; 55/514;
   55/524; 128/272; 128/275; 156/290; 156/308.4;
   229/DIG. 14; 210/436; 210/472; 210/927
[58] Field of Search ..................... 55/385 C, 514, 524,
   55/527, 528; 210/472, 436, 927; 156/290, 293,
   308.4; 128/275, 272; 229/DIG. 14

[56] References Cited

U.S. PATENT DOCUMENTS 3,575,170 4/1971 Clark .................................. 128/275
3,803,810 4/1974 Rosenberg ............................ 55/527
4,120,715 10/1978 Ockwell et al. .................... 156/290

Primary Examiner—Bernard Nozick
Attorney, Agent, or Firm—Roger A. Williams

[57] ABSTRACT

An improved method for attaching a hydrophobic vent directly to a urinary drainage container without requiring special supplemental donut-shaped sandwich structures for retaining the filter. The substantially improved fusion bond is obtained by a special seal structure formed by a die having two protruding fusion ribs separated by a relief groove. The seal structure formed by such a die permits direct sealing of a silicone treated hydrophobic vent to a thermoplastic bag wall with a firm viable seal.

10 Claims, 4 Drawing Figures

MEDICAL LIQUID CONTAINER WITH FILTER VENT

This is a continuation of application Ser. No. 936,754 filed Aug. 25, 1978 now abandoned.

BACKGROUND

It is highly desirable in urinary drainage bags to have a hydrophobic vent through the bag wall so that air flowing from a urinary drainage tube can vent through the bag and permit the bag to become filled with urine. These hydrophobic vents permit the air to exit from the bag, and yet do not leg liquid flow out of the vent. The hydrophobic vents are of a special water repellent, sometimes called "non-wetting" construction. They are often coated with silicone oil to help in their water repellency, air passage, and performance.

Because of their water repellent and somewhat slippery nature, hydrophobic filters are extremely difficult to seal to a bag wall in a liquid-tight seal. Various attempts have been proposed to confine the filter between a donut structure of a material that is readily bondable to the urine bag wall by fusion. Examples of such structure are disclosed in U.S. Pat. Nos. 3,557,170; 3,943,929; 3,952,727; and 3,998,255. Each of these patents require expensive, separately cut and handled donut-shaped holders for the filter material.

SUMMARY OF THE INVENTION

The present invention provides an improved seal structure that was unexpectedly found to substantially increase the sticking power of a hydrophobic filter directly to a thermoplastic film of a urinary drainage container or the like. This seal structure and the die for forming it eliminates the need for the donut-shaped retainers, and provides a very simple and reliably strong seal between the filter and the container or bag wall. The seal structure includes two fused anchoring areas separated by a relief area. This seal structure is formed by a die having two protruding ribs separated by a relief groove, and preferably each rib extends about the periphery of the vent opening in the bag wall.

THE DRAWINGS

FIG. 5 is a sectional view taken along line 5—5 of FIG. 2.

DETAILED DESCRIPTION

Figure 1:
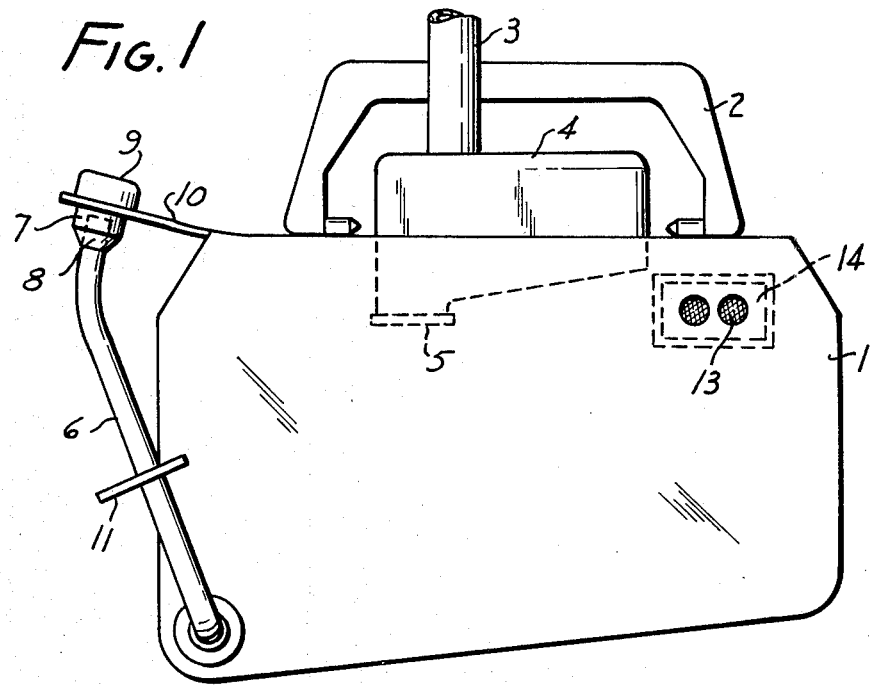
FIG. 1 is a front elevational view of a urinary drainage bag with the filter sealed to an inner surface of the bag.

FIG. 1 shows a urinary drainage bag 1, which can be made of polyvinylchloride film and to this bag is attached a handle 2. A urinary drainage line 3 enters a drip housing 4 which has an outlet valve 5 entering the bag. Preferably, a bottom emptying drainage tube 6 has an outer enlarged protector 7 which protects a drip tube 8 when emptying the bag through tube 6. A cap 9 can be integrally secured to a top of the bag with a web 10 for holding the tube in the position shown. A clamp 11, such as a slide clamp, is shown for opening and closing tube 6. Other types of pinch clamps could be used, if desired.

The current invention relates to the area of the bag in which a vent opening 13 is shown. In FIG. 1, two vent openings are shown positioned side by side. However, other single or multiple vent openings could be used as desired. Sealed against an inner surface of the bag wall is a hydrophobic filter 14. A "hydrophobic" filter means a filter which will permit the exit of air from the bag, but will not let liquid pass through the filter passages where the urine in the bag may come in contact with contaminated outer surfaces of the bag.

Figure 2:
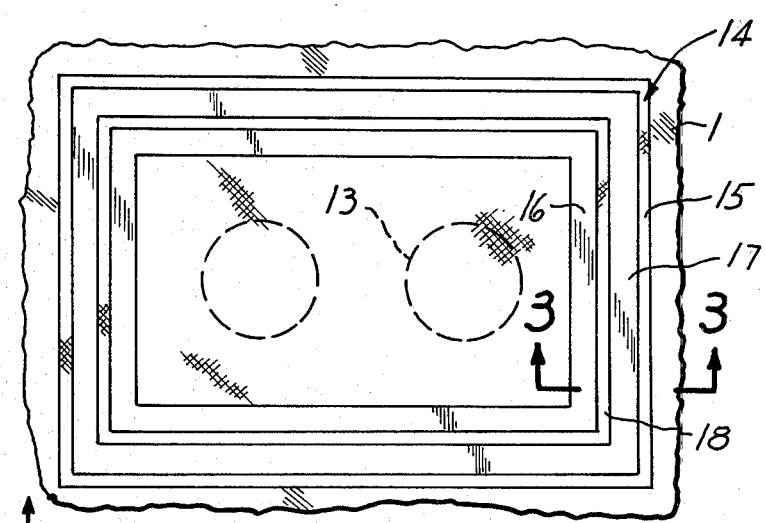
FIG. 2 is an enlarged fragmentary view of the filter as seen from inside the bag.

FIG. 2 is a view from an inner surface of the bag wall of FIG. 1 showing the seal structure of the filter 14 to bag wall 1. As shown in FIG. 2, the filter 14 is superimposed on the bag wall because the viewer is considered to be looking at the filtered covered vent from inside the bag. This is why the vent openings 13 are shown in dotted as being on the opposite side of the filter 14. The filter 14 has an outer unsealed periphery 15 which is formed by the filter being cut slightly oversize for the sealing die to insure the filter is always as large as or slightly larger than the die. The filter is sealed to the bag wall by a pair of generally parallel anchoring areas 16 and 17 which preferably are in rectangular shape, and each extending about the periphery of an area of the bag wall defining its vent openings, such as 13. Between anchoring areas 16 and 17 is a relief area 18 that is secured, if at all, to the bag wall by only a very light tack seal. The holding power for the fusion joint between the filter 14 and bag 1 is concentrated in the anchoring areas 16 and 17 which have a width of 0.010 to 0.60 inch.

The applicant had previously tried to seal a hydrophobic filter material directly to a urinary bag wall using a single wide sealing area about the periphery of the filter, and such sealing area was approximately equivalent to the combined anchoring areas and relief areas shown in FIG. 2. Such seal structure was unsuccessful because the filter could be readily pealed off of the bag wall after sealing. A die with a central relief groove was made in an effort to better determine how the seal structure functions and why it was failing. One would normally expect that the relief groove in the sealing die, which formed the relief area between the two anchoring areas of the seal, would still further decrease the sticking power of the filter to the bag wall because there was less area doing the holding. Unexpectedly, this was found to be just the opposite of what occurred. By incorporating the relief area 18 in the seal, its holding power was approximately doubled. This, for the first time, permitted a hydrophobic filter to be reliably sealed directly to the bag wall without the expensive donut holder construction surrounding the filter.

Why this improved seal takes place with this construction is not entirely known. It may be that when the anchoring areas 16 and 17 are formed, the relief area 18 permits a slight swelling up of displaced wall material from the anchoring areas as the fusion joint is made. Perhaps this reduces the lateral stretching and shearing effect at the interface between the filter and bag wall as the seal is made.

Figure 3:
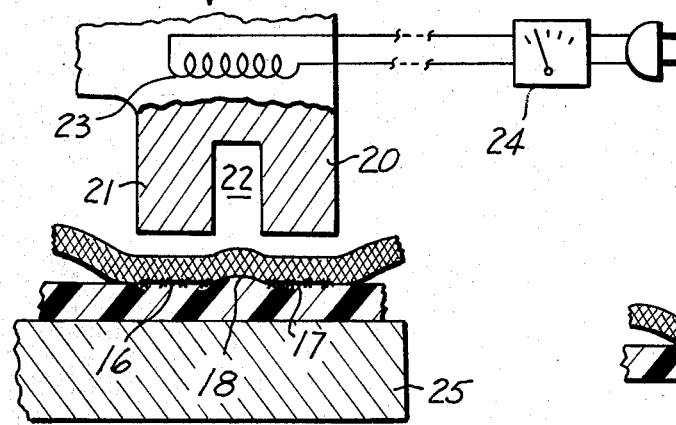
FIG. 3 is an enlarged fragmentary view showing a cross-sectional shape of a forming die for the seal showing a first embodiment of the seal construction where there is a slight weakened tack in a central relief section of the seal.

FIG. 3 shows a schematic drawing of the heating die which includes a protruding rib 20 and a similar rib 21 separated by a relief groove 22. Ribs 20 and 21 each have a width of 0.010 to 0.060 inch. The heating die has a means schematically shown at 23 for heating the die to 175° to 225° F. and a control means 24 for regulating this temperature. It is understood that the heater can be in a support housing which can conduct heat to the particular die. The heater need not be in the die itself. There is also a means, such as hydraulics, air actuated, etc., for moving the die in repetitive strokes up and down relative to a base 25. Preferably, the die is also connected to a R.F. (radio frequency) energy source to aid in making the seal. Since both R.F. and conductive heat dies and the mechanical operating structure for them are known, the specific details of such tools have been shown only schematically.

Figure 4:
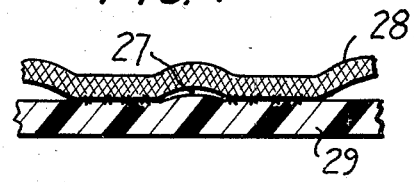
FIG. 4 is a second embodiment of the seal construction where the central relief section of the seal is unfused to the bag wall.

In a first embodiment of the seal structure shown in FIG. 3, the relief area at 18 exhibits only a slightly tack area forming a substantially weaker joint in this area than in the anchoring areas 16 and 17. In a second embodiment of the seal structure in FIG. 4, the relief area at 27 is shown with a very slight space between the filter 28 and bag wall 29. It has been found that both of these seal constructions shown in FIGS. 3 and 4 work exceptionally well, and through slight manufacturing tolerances, sometimes the seal will be made as shown in FIG. 3, and at other times as shown in FIG. 4.

With the above seal construction, a hydrophobic filter of an extremely slippery material, such as a teflon coated fabric which might also include a silicone oil surface treatment to render the filter water repellent, is bondable in a secure fusion joint to a urinary bag wall. It is believed that the two spaced apart anchoring areas separated by a relief area help compress thermoplastic material of the bag wall into the minute pores of the filter material for a firm seal. The FIGS. 3 and 4 cross-section of the die and seal structure preferably extend around the complete perimeter of the seal, and it is understood that the die would have an overall rectangular shape as shown in the seal made by such a die in FIG. 2.

In the foregoing description, specific examples have been used to describe the invention. However, it is understood by those skilled in the art that certain modifications can be made to these examples without departing from the spirit and scope of the invention.

I claim:

1. A medical liquid container having a thermoplastic wall with a filter which comprises a material different than the wall material and which covers a vent opening in the wall, wherein the improvement comprises: a direct face to face contact zone between the filter and wall about the vent opening wherein the two different materials of the wall and filter are in contact with each other; and a liquid-tight seal in the contact zone that includes a plurality of permanently fused anchor areas separated by a relief area, which anchor areas are at a common interface between the two different materials of the wall and filter within the contact zone.

2. A medical liquid container as set forth in claim 1, wherein the anchor areas each have a width of from 0.010 to 0.060 inch.

3. A medical liquid container as set forth in claim 1, wherein there is a light fusion between the filter and wall in the relief area, but such fusion is substantially weaker than in the permanently fused anchor areas.

4. A medical liquid container as set forth in claim 1, wherein the filter and wall are substantially unfused in the relief area.

5. A medical liquid container as set forth in claim 1, wherein the anchor areas include two generally parallel fusion seals, each extending about the vent opening.

6. A medical liquid container as set forth in claim 5, wherein the fusion seals are generally rectangular.

7. A medical liquid container as set forth in claim 1, wherein the filter is hydrophobic.

8. A medical liquid container as set forth in claim 7, wherein the filter has a water repellent coating.

9. A medical liquid container as set forth in claim 8, wherein the water repellent coating is silicone oil.

10. A urine collection bag having a flexible thermoplastic wall with a flexible hydrophobic filter of a material different than the material of the thermoplastic wall and covering a vent opening in the wall, wherein the improvement comprises: a direct face to face contact zone between the hydrophobic filter and an inner surface of the wall; a water repellent coating on the filter in the contact zone wherein the coated filter and thermoplastic wall of differing materials are in contact with each other; and a liquid-tight seal in the contact zone that includes a pair of permanently fused anchor seals separated by a relief area, which anchor seals are at a common interface between the two different materials of the wall and filter.

* * * * *

UNITED STATES PATENT AND TRADEMARK OFFICE
CERTIFICATE OF CORRECTION

PATENT NO. : 4,356,012
DATED : October 26, 1982
INVENTOR(S) : Jack H. Hofstetter It is certified that error appears in the above-identified patent and that said Letters Patent are hereby corrected as shown below:

Column 1, line 14, change "leg" to -- let --.

Column 2, line 36, change "0.60" inch to -- 0.060 -- inch.

Signed and Sealed this

Eleventh Day of January 1983

[SEAL]

Attest:

GERALD J. MOSSINGHOFF

Attesting Officer     Commissioner of Patents and Trademarks